US00PP27660P2

(12) United States Plant Patent
Jennings

(10) Patent No.: US PP27,660 P2
(45) Date of Patent: Feb. 14, 2017

(54) ***RUBUS* PLANT NAMED 'GLEN DEE'**

(50) Latin Name: *Rubus idaeus*
Varietal Denomination: Glen Dee

(71) Applicant: Sophia N. Jennings, Abernethy (GB)

(72) Inventor: Sophia N. Jennings, Abernethy (GB)

(73) Assignee: JAMES HUTTON INSTITUTE OF SCOTLAND, Dundee, Scotland (GB)

( * ) Notice: Subject to any disclaimer, the term of this patent is extended or adjusted under 35 U.S.C. 154(b) by 182 days.

(21) Appl. No.: 14/121,308

(22) Filed: Aug. 18, 2014

(51) Int. Cl.
*A01H 5/08* (2006.01)

(52) U.S. Cl.
USPC ..... Plt./204

(58) Field of Classification Search
USPC ..... Plt./204
See application file for complete search history.

*Primary Examiner* — Keith Robinson
(74) *Attorney, Agent, or Firm* — Penny J. Aguirre

(57) ABSTRACT

A new cultivar of *Rubus idaeus*, 'Glen Dee', that is characterized by its spinefree canes, its fruit that is large in size with a good, palatable flavor and high Brix°, its $A_{10}$ resistance to the European raspberry aphid (*Amphorophora idaei*), its field tolerance to the raspberry bushy dwarf virus (*Idaeovirus* RBDV) and raspberry root rot (*Phytophthora rubi*), and its late fruiting season.

2 Drawing Sheets

Botanical classification: *Rubus idaeus.*
Cultivar designation: 'Glen Dee'.

BACKGROUND OF THE INVENTION

The present invention relates to a new and distinct cultivar of raspberry plant, botanically known as *Rubus idaeus* 'Glen Dee' and will be referred to hereinafter by its cultivar name, 'Glen Dee'.

The new cultivar was derived from a controlled breeding program in Dundee, Scotland. The objectives of the breeding program are to develop new raspberry cultivars suitable for the fresh fruit market that are well adapted to production under protected cropping systems with improved agronomic qualities and increased tolerance to pathogens. The Inventor made a cross in 2004 between unnamed proprietary plants in the Inventor's breeding program, reference no. MRS 00123A5 as the female parent and reference no. MRS 0019B11 as the male parent. The Inventor selected 'Glen Dee' in 2006 as a single unique plant amongst the seedlings that resulted from the above cross.

Asexual propagation of the new cultivar was first accomplished by the Inventor by root cuttings in Dundee, Scotland in 2006. Asexual propagation by root cuttings and tissue culture has shown that the unique features of the new cultivar are stable and reproduced true to type in successive generations.

SUMMARY OF THE INVENTION

The following traits have been repeatedly observed and represent the characteristics of the new cultivar. These attributes in combination distinguish 'Glen Dee' as a new and unique cultivar of *Rubus*.

1. 'Glen Dee' exhibits spine free canes.
2. 'Glen Dee' exhibits fruit that is large in size.
3. 'Glen Dee' exhibits good flavor with a high Brix°.
4. 'Glen Dee' exhibits $A_{10}$ resistance to the European raspberry aphid (*Amphorophora idaei*).

5. 'Glen Dee' has been observed to be free of raspberry bushy dwarf virus (RBDV) in Scotland.
6. 'Glen Dee' exhibits good root vigor and some field tolerance to raspberry root rot (*Phytophthora rubi*).
7. 'Glen Dee' exhibits a late summer fruiting season.

The parents of, 'Glen Dee', MRS 00123A5 and MRS 0019B11, differ from 'Glen Dee' in having fruit that is smaller in size, in having an earlier fruiting season, in having decreased tolerance to raspberry root rot (*Phytophthora rubi*), and in being less resistant to European large raspberry aphid (*Amphorophora idaei*). 'Glen Dee' can also be compared to the raspberry cultivars 'Tulameen' (not patented) and 'Glen Ample' (U.S. Plant Pat. No. 11,418). 'Tulameen' is similar to 'Glen Dee' in having fruit that is large in size with a palatable flavor. 'Tulameen' differs from 'Glen Dee' in having spines on its canes, in having an earlier fruiting season, and in having fruit that is dark red in color. 'Glen Ample' is similar to 'Glen Dee' in having spine free canes. 'Glen Ample' differs from 'Glen Dee' in having fruit that is smaller in size and in having an earlier fruiting season.

BRIEF DESCRIPTION OF THE DRAWINGS

The accompanying colored photographs illustrate the overall appearance and distinct characteristics of the new *Rubus*, 'Glen Dee'. The photographs were taken in Dundee, Scotland of a 4 year-old plant as grown outdoors in the ground.

The photograph in FIG. 1 provides a view of the habit of a plant of 'Glen Dee'.

Figure 1:
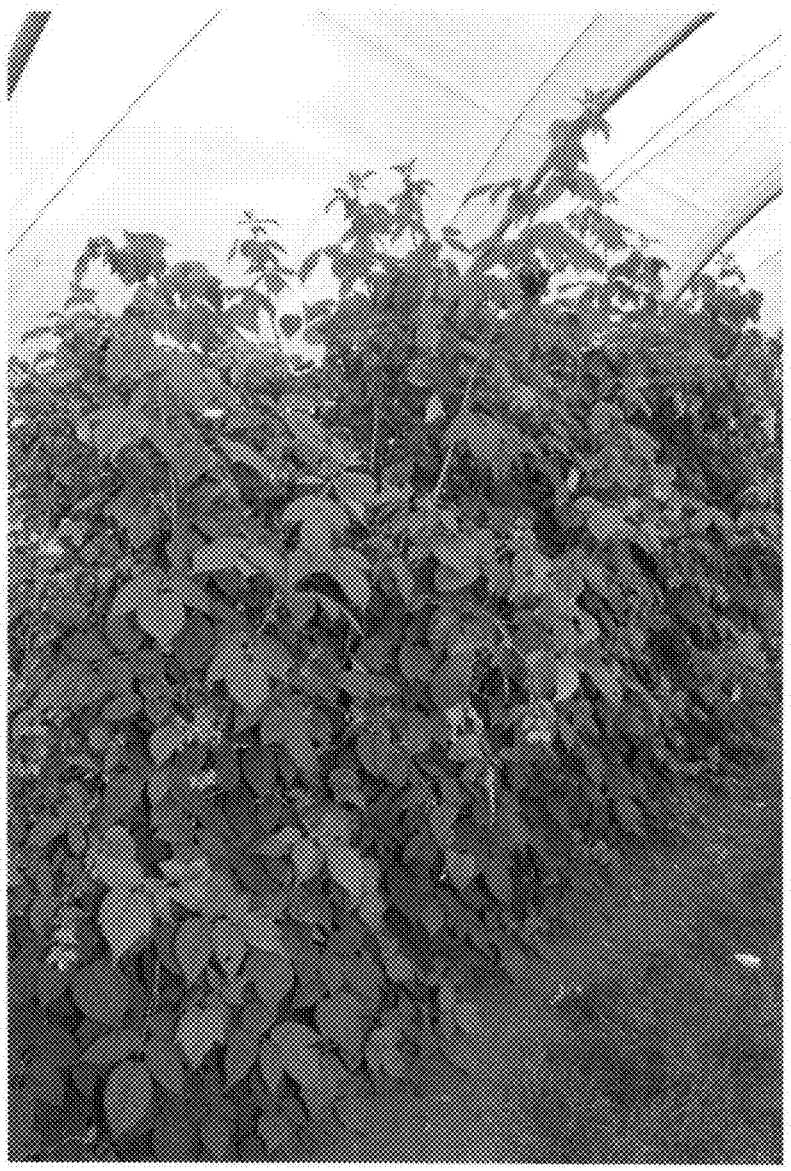
Figure 2:
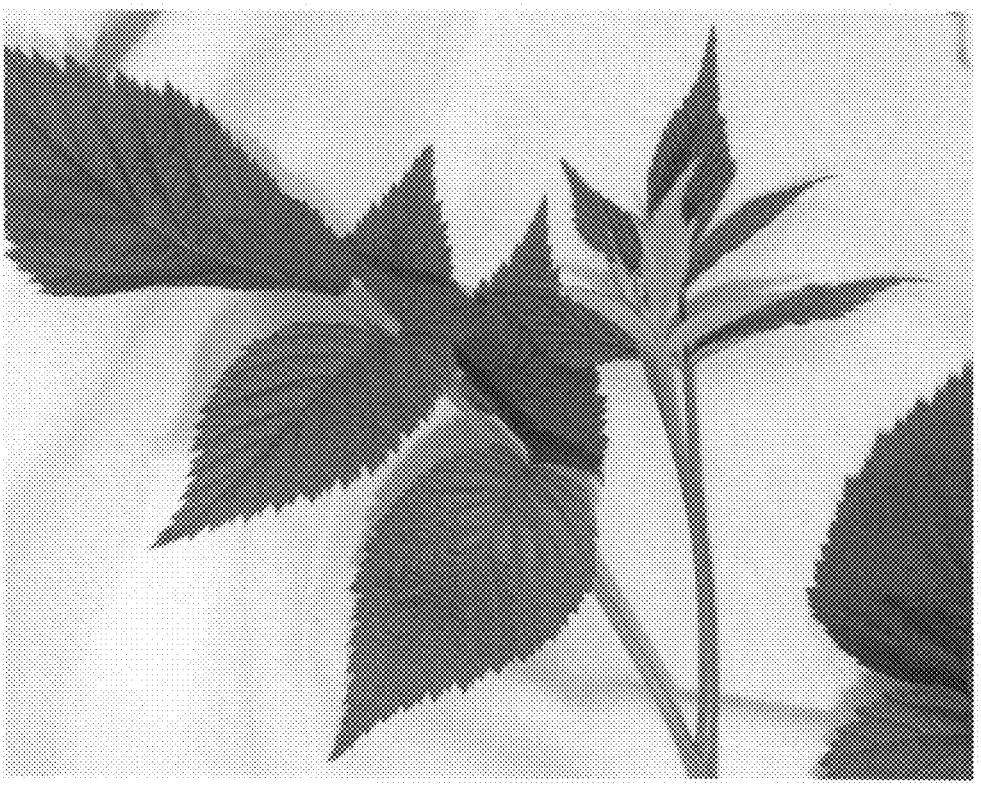

The photograph in FIG. 2 provides a close-up view of the leaves of 'Glen Dee'.

Figure 3:
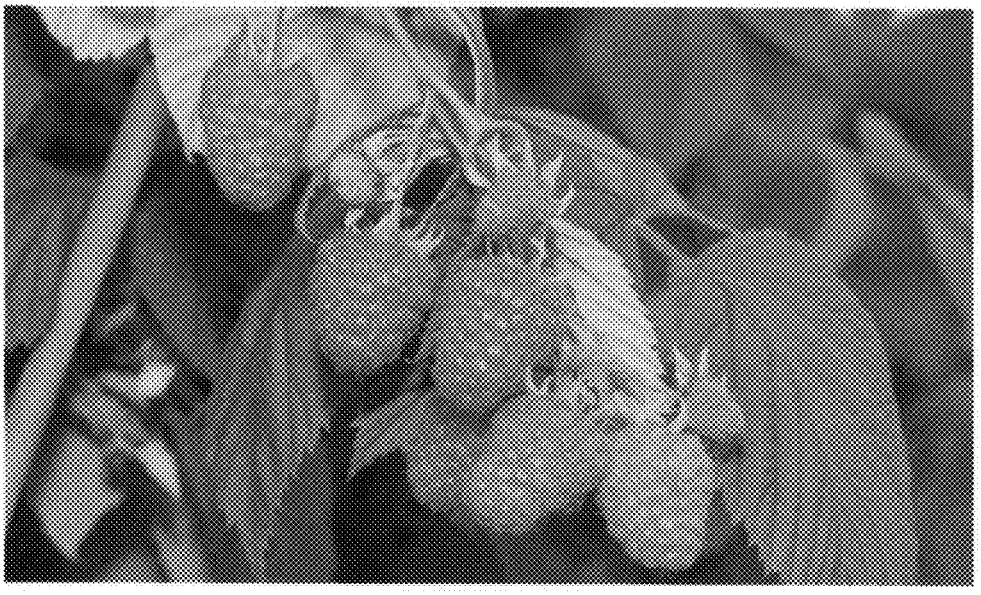

The photograph in FIG. 3 provides a close-up view of the fruits of 'Glen Dee'.

The colors in the photographs are as close as possible with the photographic and printing technology utilized. The colors in the photograph may differ slightly from the color values cited in the detailed botanical description, which accurately describe the colors of the new *Rubus*.

DETAILED BOTANICAL DESCRIPTION OF THE PLANT

The following is a detailed description of 4 year-old plants of the new cultivar as grown outdoors in the ground in Dundee, Scotland. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Mid-late season; flowering late May-early July in Scotland.

*Plant habit*.—Perennial, upright to semi-upright.

*Height and spread*.—Primocane canes reach up to 2.5 m height, spreading of 1 m.

*Hardiness*.—At least U.S.D.A. Zone 9a.

*Diseases and pests*.—Resistant to the European raspberry aphid (*Amphorophora idaei*), tolerant to raspberry bushy dwarf virus (*Idaeovirus* RBDV) and some field tolerance to raspberry root rot (*Phytophthora rubi*).

*Root description*.—Fibrous and vigorous.

*Branching habit*.—Not freely branching.

*Propagation*.—Root cuttings (preferred) or tissue culture.

*Growth rate*.—Moderate to vigorous.

Cane description (new growth; primocanes, mature canes; floricanes):

*Cane size*.—An average of 2.3 m in length and 8 cm in width at mid stem.

*Stem color*.—144A.

*Stem surface*.—New growth; glabrous without spines or prickles, color 165A.

*Stipules*.—2 per petiole, very fine, an average of 7 mm in length, lanceolate in shape, color 145A.

Foliage description:

*Time of vegetative bud burst*.—Mid to late April in Scotland.

*Leaf shape*.—Ovate in overall form.

*Leaf division*.—3 leaflets (occasionally 5).

*Leaf attachment*.—Petiolate.

*Leaf orientation*.—Outward to pendant.

*Leaf size*.—An average of 20 cm in length and 16.5 cm in width.

*Leaf quantity*.—An average of 13 per stem.

*Internode length*.—An average of 7 cm.

*Leaflet shape*.—Ovate.

*Leaflet base*.—Terminal leaflets; cordate to cuneate, lateral leaflets; oblique.

*Leaflet apex*.—Acute.

*Leaflet venation*.—Pinnate, color primarily matches leaf color.

*Leaflet margins*.—Doubly serrate.

*Leaflet arrangement*.—One terminal and 1 to 2 lateral pairs, not overlapping (free).

*Leaflet attachment*.—Sessile.

*Leaflet surface*.—Upper and lower surface slightly rugose.

*Leaflet color*.—Upper surface 134A, lower surface 191A.

*Leaflet size*.—Terminal; an average of 11.5 cm in length and 8.8 cm in width, lateral; and average of 8 cm in length and 5 cm in width.

*Leaflet substance*.—Thin.

*Petioles*.—Round in shape, an average of 5 cm in length and 1.5 mm in width, color 146D, surface pubescent and without spines/prickles.

*Rachis*.—Round in shape, an average of 9 cm in length and 0.8 mm in width, color; sun exposed surface 144B to 144D, upper surface suffused with 173A and shaded surface 145A, all surfaces pubescent and without spines/prickles.

Inflorescence description:

*Inflorescence*.—Raceme, an average of 8 cm in length (from base of rachis) and 1.5 cm in width.

*Lastingness of inflorescence*.—About 4 days.

*Rachis* (*peduncle*).—Oval in shape, color N144A, glabrous surface, without spines/prickles, an average of 14 cm in length and 2 mm in width.

*Pedicels*.—Oval in shape, an average of 2.2 cm in length and 1 mm in width, color 146D, surface glabrous without spines/prickles.

*Flower buds*.—Triangular in shape with a flat wide bottom and apex narrowing to a point, up to 7 mm in width and 6 mm in length, color 144B.

*Flower type*.—Spreading calyx with a center of a ring of numerous upright stamens and with numerous pistils in the center, petals are quickly shed upon opening.

*Flower number*.—An average of 7 per raceme.

*Flower size*.—Average of 9 mm in depth and 2.2 cm in diameter.

*Sepals*.—Five, an average of 1 cm in length and 5mm in width, base cuneate, apex lanceolate, smooth on both surfaces.

*Petals*.—Five, dropped just after flower opening, an average of 5 mm in length and 2.9 mm in width, obovate in shape with a rounded apex and cuneate base, glabrous on upper and lower surfaces, thin, color NN155B.

*Receptacle*.—An average of 8.5 mm in diameter and 15.9 mm in depth, color 155D.

*Androecium*.—An average of 80 stamens that form a concentric ring about 9 mm in diameter, inserted into calyx at base, about 5.2 mm in length. Filament color NN155C, anthers <1 mm in length, color 163C, pollen was not observed.

*Gynoecium*.—An average of 72 pistils, styles are an average of 5 mm in length and color 155B, stigmas are very small, ovaries are attached to receptacle at base, about 3.7 mm in length and 4 mm in width, ovate in shape, and color 157C.

Fruit description:

*Fruit number*.—An average of 20 per fruiting branch.

*Fruit size*.—Aggregate an average of 2.5 cm in diameter and 2.7 cm in length.

*Fruit shape*.—Aggregate fruit is broad conical.

*Drupelets*.—An average of 72 per aggregate fruit, globose in shape, firm, an average of 4.5 mm in diameter and height, color when maturing; 148C, color when mature; 45B, surface has low glossiness, style and stigma; persistent at maturity, fine.

*Persistence of bracts*.—Persistent.

*Receptacle*.—Round in shape (sits on calyx), stamens are inserted in the perimeter and ovaries are adhered in the center, an average of 8 mm in diameter and 1.6 mm in depth, 158B in color on upper and lower surface.

*Fruit maturity date*.—Late summer in Scotland.

*Seed*.—Oval in shape, 1 per drupelet, 3 mm in length, 1.5 mm in width, 164B in color.

*Cropping frequency*.—Annually, produced on 1-year-old wood (floricanes) in the summer.

*Flavor*.—Sweet tart.

*BRIX*.—10.5°.

*Fruit weight*.—Average of 5.8 g.

It is claimed:

1. A new and distinct cultivar of *Rubus* plant named 'Glen Dee' as herein illustrated and described.

* * * * *